United States Patent

Koike et al.

[11] 4,254,262
[45] Mar. 3, 1981

[54] PROCESS FOR PRODUCING PHENOXYCARBOXYLIC ACID DERIVATIVE

[75] Inventors: Wataro Koike; Tadashi Sasuga, both of Shizuoka; Chihiro Yazawa, Yokohama, all of Japan

[73] Assignee: Ihara Chemical Industry Co., Ltd., Tokyo, Japan

[21] Appl. No.: 84,164

[22] Filed: Oct. 12, 1979

[30] Foreign Application Priority Data

Nov. 1, 1978 [JP] Japan ................. 53-135060

[51] Int. Cl.³ .............. C07D 213/57; C07C 61/08; C07C 69/767
[52] U.S. Cl. .................. 546/287; 546/288; 546/297; 546/301; 546/302; 546/303; 560/61; 562/471
[58] Field of Search .................. 560/61; 562/471; 546/288, 287, 297, 301, 302, 303, 25

[56] References Cited

U.S. PATENT DOCUMENTS

| | | | |
|---|---|---|---|
| 3,968,143 | 7/1976 | Schacht et al. | 562/471 |
| 3,972,887 | 8/1976 | Freedman | 546/25 |

OTHER PUBLICATIONS

Eastman Organic Chemical Bulletin, pp. 1–3, vol. 48(1), 1976.

Primary Examiner—Alan L. Rotman
Attorney, Agent, or Firm—Oblon, Fisher, Spivak, McClelland & Maier

[57] ABSTRACT

A phenoxycarboxylic acid derivative having the formula

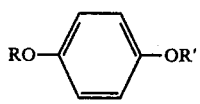

(III)

wherein R represents

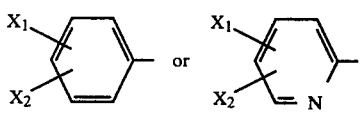

and $X_1$ represents a hydrogen atom, a halogen atom, a lower alkyl group, trifluoromethyl group, nitro group or cyano group and $X_2$ represents a hydrogen atom, a halogen atom, a lower alkyl group, nitro group or cyano group, R' represents

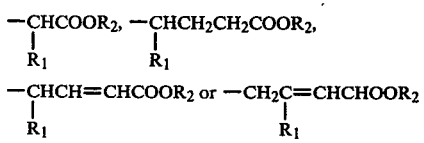

and $R_1$ and $R_2$ are the same and different and respectively represent hydrogen atom or a lower alkyl group, is produced by reacting a phenol compound having the formula

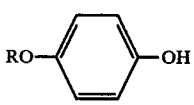

(I)

with a halogen compound having

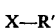

wherein X represents a halogen atom in the presence of a base. The reaction is carried out in the presence of a quarternary ammonium salt or a quaternary phosphonium salt in a nonpolar solvent.

2 Claims, No Drawings

PROCESS FOR PRODUCING PHENOXYCARBOXYLIC ACID DERIVATIVE

BACKGROUND OF THE INVENTION

1. Field of the Invention

The present invention relates to a process for producing phenoxycarboxylic acid derivatives useful as agricultural chemicals.

2. Description of the Prior Arts

It has been known that phenoxycarboxylic acid derivatives can be produced by reacting a phenol compound having the formula

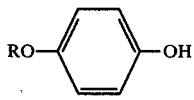

wherein R represents

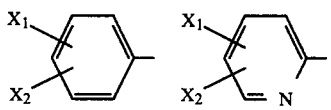

and $X_1$ represents a hydrogen atom, a halogen atom, a lower alkyl group, trifluoromethyl group, nitro group or cyano group; $X_2$ represents a hydrogen atom, a halogen atom, a lower alkyl group, nitro group or cyano group, with a halogen compound having the formula X—R'
wherein R' represents

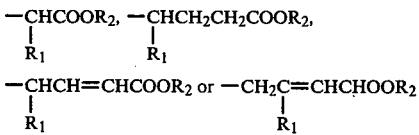

and $R_1$ and $R_2$ respectively represent a hydrogen atom or a lower alkyl group and X represents a halogen atom, in a solvent such as ketones e.g. acetone, butanone and methyl ethyl ketone; ethers e.g. tetrahydrofuran, diethyl ether, methyl butyl ether, ethyleneglycol dimethyl ether; dimethylformamide, dimethylacetamide, dimethylsulfoxide, benzene, toluene and hexane, in the presence of a dehydrogenhalide agent of an alkali metal compound such as sodium or potassium compound or an alkaline earth metal compound such as calcium or magnesium compound. This is disclosed in Japanese Unexamined Patent Publication No. 22432/1973, 125228/1976, 32730/1976, and 87173/1977.

However, a dehydrogenhalidation of the halogen compound is caused by this process. Thus, a large amount of the halogen compound should be used and a large amount of the by-products is produced to cause low yield of the object compound.

The inventors have studied to obtain a phenoxycarboxylic acid derivative having high purity in high yield.

SUMMARY OF THE INVENTION

It is an object of the present invention to provide a process for producing a phenoxycarboxylic acid derivative having high purity in high yield by preventing side reactions.

The foregoing and other objects of the present invention have been attained by reacting a phenol compound having the formula

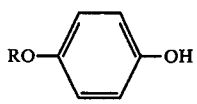

(I)

wherein R represents

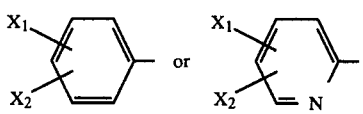

and $X_1$ represents a hydrogen atom, a halogen atom, a lower alkyl group, trifluoromethyl group, nitro group or cyano group; $X_2$ represents a hydrogen atom, a halogen atom, a lower alkyl group, nitro group or cyano group, with a halogen compound having the formula X—R'     (II)
wherein R' represents

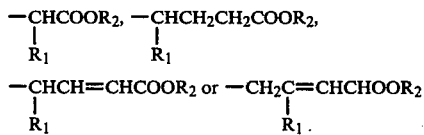

and $R_1$ and $R_2$ respectively represent a hydrogen atom or a lower alkyl group; and X represents a halogen atom, in the presence of a quaternary ammonium salt or a quaternary phosphonium salt and in the presence of a base of an alkali metal compound or an alkaline earth metal compound to produce a phenoxycarboxylic acid derivative having the formula

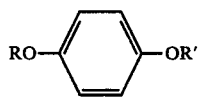

(III)

wherein R and R' are defined above.

DETAILED DESCRIPTION OF THE PREFERRED EMBODIMENTS

The phenol compounds having the formula (I) used in the present invention are the compounds having the formula

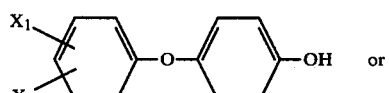

or

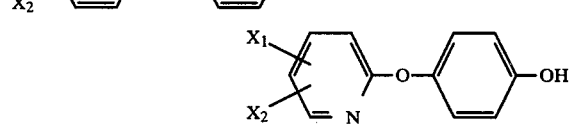

wherein $X_1$ and $X_2$ is the same or different and respectively represents a hydrogen atom; a halogen atom such as chlorine, bromine, fluorine or iodine atom; a lower alkyl group such as methyl, ethyl, i-propyl or t-butyl group; trifluoromethyl group; nitro group; or cyano group.

Suitable phenol compounds (I) include 4-phenoxyphenol, 4-(2-chlorophenoxy)phenol, 4-(4-chlorophenoxy)phenol, 4-(4-bromophenoxy)phenol, 4-(3-methylphenoxy)phenol, 4-(4-methylphenoxy)phenol, 4-(3-trifluoromethylphenoxy)phenol, 4-(4-trifluoromethylphenoxy)phenol, 4-(2,5-dichlorophenoxy)phenol, 4-(3,4-dichlorophenoxy)phenol, 4-(3,5-dichlorophenoxy)phenol, 4-(4-chloro-3-methylphenoxy)phenol, 4-(4-chloro-2-methylphenoxy)phenol, 4-(2-bromo-4-trifluoromethylphenoxy)phenol, 4-(2-chloro-4-trifluoromethylphenoxy)phenol, 4-(4-chloro-2-nitrophenoxy)phenol, 4-(4-chloro-2-cyanophenoxy)phenol, 4-(5-methyl-2-isopropylphenoxy)phenol, 4-(4-trifluoromethyl-2-nitrophenoxy)phenol, 4-(2-cyano-4-trifluoromethylphenoxy)phenol, 4-(4-cyano-2-nitrophenoxy)phenol, 4-(5-chloropyridyl-2-oxy)phenol, 4-(5-bromopyridyl-2-oxy)phenol, 4-(5-iodopyridyl-2-oxy)phenol, 4-(3,5-dichloropyridyl-2-oxy)phenol, 4-(3,5-dibromopyridyl-2-oxy)phenol and 4-(3,5-diiodopyridyl-2-oxy)phenol.

The halogen compounds used in the present invention are the compounds having the formula (II) wherein R' represents

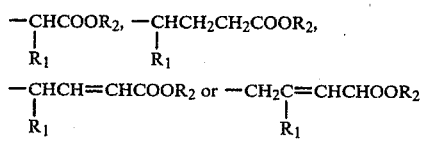

and $R_1$ and $R_2$ respectively represent a hydrogen atom; a lower alkyl group such as methyl, ethyl, n-propyl, i-propyl, n-butyl, or i-butyl group; X represents a halogen atom such as chlorine, bromine or iodine atom.

Suitable halogen compounds (II) include 2-bromopropanoic acid, 2-chloropropanoic acid, methyl 2-bromopropanoate, ethyl 2-bromopropanoate, ethyl 2-chloropropanoate, propyl 2-bromopropanoate, propyl 2-chloropropanoate, butyl 2-bromopropanoate, butyl 2-chloropropanoate, 2-bromobutanoic acid, 2-chlorobutanoic acid, methyl 2-bromobutanoate, methyl 2-chlorobutanoate, ethyl 2-bromobutanoate, ethyl 2-chlorobutanoate, propyl 2-bromobutanoate, propyl 2-chlorobutanoate, butyl 2-bromobutanoate, butyl 2-chlorobutanoate, 2-bromopentanoic acid, 2-chloropentanoic acid, methyl 2-bromopentanoate, methyl 2-chloropentanoate, ethyl 2-bromopentanoate, ethyl 2-chloropentanoate, propyl 2-bromopentanoate, propyl 2-chloropentanoate, butyl 2-bromopentanoate, butyl 2-chloropentanoate, 4-bromopentanoic acid, 4-chloropentanoic acid, methyl 4-bromopentanoate, methyl 4-chloropentanoate, ethyl 4-bromopentanoate, ethyl 4-chloropentanoate, propyl 4-bromopentanoate, propyl 4-chloropentanoate, butyl 4-bromopentanoate, butyl 4-chloropentanoate, 4-bromohexanoic acid, 4-chlorohexanoic acid, methyl 4-bromohexanoate, methyl 4-chlorohexanoate, ethyl 4-bromohexanoate, ethyl 4-chlorohexanoate, propyl 4-bromohexanoate, propyl 4-chlorohexanoate, butyl 4-bromohexanoate, butyl 4-chlorohexanoate, 4-bromoheptanoic acid, 4-chloroheptanoic acid, methyl 4-bromoheptanoate, methyl 4-chloroheptanoate, ethyl 4-bromoheptanoate, ethyl 4-chloroheptanoate, propyl 4-chloroheptanoate, butyl 4-bromoheptanoate, butyl 4-chloroheptanoate, 4-bromo-2-pentenoic acid, 4-chloro-2-pentenoic acid, methyl 4-bromo-2-pentenoate, methyl-4-chloro-2-pentenoate, ethyl 4-bromo-2-pentenoate ethyl 4-chloro-2-pentenoate, propyl 4-bromo-2-pentenoate, propyl 4-chloro-2-pentenoate, butyl 4-bromo-2-pentenoate, butyl 4-chloro-2-pentenoate, 4-bromo-2-hexenoic acid, 4-chloro-2-hexenoic acid, methyl-4-bromo-2-hexenoate, methyl 4-chloro-2-hexenoate, ethyl 4-bromo-2-hexenoate, ethyl 4-chloro-2-hexenoate, propyl 4-bromo-2-hexenoate, propyl 4-chloro-2-hexenoate, butyl 4-bromo-2-hexenoate, butyl 4-chloro-2-hexenoate, 4-bromo-2-heptenoic acid, 4-chloro-2-heptenoic acid, methyl 4-bromo-2-heptenoate, methyl 4-chloro-2-heptenoate, ethyl 4-bromo-2-heptenoate, ethyl 4-chloro-2-heptenoate, propyl 4-bromo-2-heptenoate, propyl 4-chloro-2-heptenoate, butyl 4-bromo-2-heptenoate, butyl 4-chloro-2-heptenoate, 4-chloro-3-methyl-2-butenoic acid, 4-bromo-3-ethyl-2-butenoic acid, methyl 4-chloro-3-methyl-2-butenoate and propyl 4-bromo-3-methyl-2-butenoate.

The quaternary ammonium salts or the quaternary phosphonium salts include benzyltrialkylammonium salts, benzyltrialkylphosphonium salts, tetraalkylammonium salts, tetraalkylphosphonium salts, triphenylalkylphosphonium salts and triphenylbenzylphosphonium salts such as benzyltriethylammonium bromide, benzyltributylammonium chloride, benzyltriamylammonium chloride, benzyltrioctylammonium chloride, trioctylmethylammonium chloride, isobutyltributylammonium bromide, hexadecyltributylphosphonium bromide, tetrapropylammonium bromide, tetrabutylammonium chloride, tetraamylammonium bromide, tetraamylammonium chloride, tetrahexylammonium bromide and tetrabutylphosphonium chloride. It is preferable to select the quaternary ammonium salt or the quaternary phosphonium salt from benzyl tri-$C_1$–$C_{16}$ alkylammonium salts, tetra-$C_1$–$C_{16}$ alkylammonium salts, triphenylbenzylphosphonium salts, benzyl tri-$C_1$–$C_{16}$ alkylphosphonium salts, tetra-$C_1$–$C_{16}$ alkylphosphonium salts, and triphenyl $C_1$–$C_{16}$ alkylphosphonium salts.

The alkali metal compounds or the alkaline earth metal compounds used in the present invention are the bases such as potassium hydroxide, potassium carbonate, sodium hydroxide, sodium carbonate, calcium hydroxide and magnesium oxide. It is optimum to use sodium carbonate (bicarbonate) or potassium carbonate (bicarbonate).

It is preferable to use a solvent so as to smoothly result the reaction. It is preferable to use a solvent being stable to the alkali metal compound or the alkaline earth metal compound, and especially an insert nonpolar solvent such as aromatic or aliphatic hydrocarbons and aromatic or aliphatic halohydrocarbons.

The reaction of the present invention is carried out by reacting the phenol compound having the formula (I) with the halogen compound having the formula (II) in the presence of the quaternary ammonium salt or the quaternary phosphonium salt, and in the presence of a base of the alkali metal compound or the alkaline earth metal compound in a solvent, by heating and stirring them.

After the reaction, an oil phase is separated from the reaction mixture by a phase separation and washed with an acid and with water and treated by a distillation or a recrystallization to obtain the object compound of the phenoxycarboxylc acid derivative (III) having high purity in high yield.

The halogen compound (II) is used at a molar ratio of 1.0 to 1.5 preferably 1.05 to 1.1 based on the phenol compound (I).

The quaternary ammonium salt or the quaternary phosphonium salt is used at a molar ratio of 0.005 to 0.05, preferably 0.008 to 0.015 based on the phenol compound (I).

The base of the alkali metal compound or the alkaline earth compound is used at a molar ratio of 0.5 to 1.5 based on the phenol compound (I), in a form of an aqueous solution at a desired concentration.

The reaction temperature is in a range of 50° to 90° C. preferably 60° to 80° C. The reaction time is depending upon the reaction temperature and is usually in a range of 4 to 8 hours.

In the reaction of the phenol compound (I) with the halogen compound (II), in the present invention, the dehydrogenhalide reaction of the halogen compound itself is prevented to prevent the side reactions by using at least one of the quaternary ammonium salts and the quaternary phosphonium salts such as benzyltrialkylammonium salts, benzyltrialkylphosphonium salts, tetraalkylammonium salts, tetralkylphosphonium salts, benzyltriphenylphosphonium salts, alkyl triphenylphosphonium salts whereby the phenoxycarboxylic acid derivative (III) having high purity can be obtained in high yield.

The process of the present invention attain excellent advantages that the phenoxycarboxylic acid derivative having high purity can be easily produced in high yield and the side reaction can be remarkably decreased.

The present invention will be further illustrated by certain examples and references which are provided for purposes of illustration only and are not intended to be limiting the present invention.

EXAMPLE 1

In a reactor, 100 ml of chlorobenzene and 100 ml of water were charged and then, 95.3 g (0.375 mole) of 4-(4-trifluoromethylphenoxy)phenol, 85.4 g (0.412 mole) of ethyl 4-bromo-2-pentenoate, 39.0 g (0.281 mole) of potassium carbonate and 1.1 g (0.00375 mole) of tributylethyl ammonium bromide were added. The mixture was refluxed with stirring for 6 hours to react them, and the water phase was removed and the organic phase was washed with 5% hydrochloric acid and with water and then, chlorobenzene, ethyl 4-bromo-2-pentenoate and low boiling by-products were distilled off at 100° C. under a reduced pressure of 0.02 to 0.05 mmHg to obtain 137.0 g of ethyl 4-[4-(4-trifluoromethylphenoxy)phenoxy]-2-pentenoate. The yield was 96.0%.

EXAMPLE 2

In a reactor, 100 ml of chlorobenzene and 100 ml of water were charged and 95.3 g (0.375 mole) of 4-(4-trifluoromethylphenoxy)phenol, 73.7 g (0.412 mole) of 4-bromo-2-pentenoate, 78.0 g (0.56 mole) of potassium carbonate and 1.1 g (0.00375 mole) of tributylethylammonium bromide were added. The mixture was refluxed with stirring for 6 hours. The reaction mixture was cooled to the room temperature and conc. hydrochloric acid was added to the reaction mixture with stirring to be acidic. The water phase was separated and the organic phase was washed with water and chlorobenzene was distilled off at 100° C. under a reduced pressure of 0.02 to 0.05 mmHg to obtain 4-[4-(4-trifluoromethylphenoxy)phenoxy]-2-pentenoic acid. The yield was 91.2%.

REFERENCE 1

In accordance with the process of Example 1 except that tributylethylammonium bromide was not incorporated, the mixture was refluxed with stirring for 6 hours and the reaction mixture was cooled to the room temperature and 15.0 g (0.375 mole) of sodium hydroxide was added and the mixture was further stirred for 30 minutes and the mixture was further treated to obtain 44.5 g of ethyl 4-[4-(4-trifluoromethylphenoxy)phenoxy]-2-pentenoate. The yield was 31.2%.

REFERENCE 2

In a reactor, 100 ml of ethanol was charged and 95.3 g (0.375 mole) of 4-(4-trifluoromethylphenoxy)phenol, 85.4 g (0.412 mole) of ethyl 4-bromo-2-pentenoate and 39.0 g (0.281 mole) of potassium carbonate were added. The mixture was refluxed with stirring for 6 hours to react them. Ethanol was distilled off and 100 ml of chlorobenzene and 100 ml of water were added and the mixture was stirred at the room temperature for 30 minutes. The water phase was separated and the organic phase was washed with 5% hydrochloric acid and with water and then, chlorobenzene, ethyl 4-bromo-2-pentenoate and low boiling by-products were distilled off under a reduced pressure to obtain 10.47 g of ethyl 4-[4-(4-trifluoromethylphenoxy)phenoxy]-2-pentenoate. The yield was 73.5%.

EXAMPLES 3 TO 39

In accordance with the process of Example 1 except using the phenol compounds and the halogen compounds shown in Table 1 instead of 4-(4-trifluoromethylphenoxy)phenol and ethyl 4-bromo-2-pentenoate, each reaction was carried out. The results are shown in Table 1.

TABLE 1

| Example | Starting material Phenol compound | Halogen compound |
|---|---|---|
| 3 | 4-(4-trifluoromethylphenoxy) phenol | ethyl 4-brono-2-pentenoate |
| 4 | 4-(4-trifluoromethylphenoxy) phenol | 4-bromo-2-pentenoic acid |
| 5 | 4-(4-trifluoromethylphenoxy) phenol | 2-bromopropanoic acid |
| 6 | 4-(4-trifluoromethylphenoxy) phenol | ethyl 4-chloropentanoate |
| 7 | 4-(4-trifluoromethylphenoxy) phenol | ethyl 4-bromo-2-heptenoate |
| 8 | 4-(4-trifluoromethylphenoxy) phenol | octyl 4-bromo-2-pentenoate |
| 9 | 4-(3-trifluoromethylphenoxy) phenol | ethyl 4-bromo-2-pentenoate |
| 10 | 4-(2-chloro-4-trifluoromethylphenoxy) phenol | 4-chloro-2-pentenoic acid |
| 11 | 4-(2-nitro-4-trifluoromethylphenoxy) phenol | ethyl 4-bromo-2-pentenoate |
| 12 | 4-(2-bromo-4-trifluoromethylphenoxy) phenol | ethyl 4-bromo-2-pentenoate |
| 13 | 4-phenoxyphenol | 4-bromo-2-pentenoic acid |
| 14 | 4-(2-chlorophenoxy) phenol | butyl 4-bromo-2-pentenoate |
| 15 | 4-(4-cyanophenoxy) phenol | ethyl 4-bromo-2-pentenoate |
| 16 | 4-(2,4-dichlorophenoxy) phenol | ethyl 2-chloropropanoate |
| 17 | 4-(2-nitro-4-chlorophenoxy) phenol | isopropyl 2-bromopropanoate |
| 18 | 4-(2-chloro-4-nitrophenoxy) phenol | ethyl 2-bromoacetate |
| 19 | 4-(2-nitro-4-chlorophenoxy) phenol | ethyl 4-bromo-2-butenoate |

TABLE 1-continued

| Example | Starting material Phenol compound | Halogen compound |
|---|---|---|
| 20 | 4-(4-nitrophenoxy) phenol | ethyl 2-bromobutanoate |
| 21 | 4-(4-bromophenoxy) phenol | isopropyl 4-bromo-2-pentenoate |
| 22 | 4-(3,5-dichloropyridyl-2-oxy) phenol | ethyl 2-bromopropanoate |
| 23 | 4-(3,5-dichloropyridyl-2-oxy) phenol | butyl 4-bromo-2-pentenoate |
| 24 | 4-(5-nitropyridyl-2-oxy) phenol | ethyl 2-bromopropanoate |
| 25 | 4-(5-nitropyridyl-2-oxy) phenol | ethyl 4-bromo-2-pentenoate |
| 26 | 4-phenoxyphenol | methyl 4-chloro-3-methyl-2-butenoate |
| 27 | 4-(4-chlorophenoxy) phenol | isopropyl 4-bromo-3-methyl-2-butenoate |
| 28 | 4-(5-methyl-2-isopropylphenoxy) phenol | 2-chloropropanoic acid |
| 29 | 4-(3-methylphenoxy) phenol | 2-chloropropanoic acid |
| 30 | 4-(4-chloro-3-methylphenoxy) phenol | 2-chloropropanioc acid |
| 31 | 4-(4-trifluoromethylphenoxy) phenol | isobutyl 2-bromopropanoate |
| 32 | 4-(2-bromo-4-trifluoromethylphenoxy) phenol | ethyl 2-bromopropanoate |
| 33 | 4-(5-bromopyridyl-2-oxy) phenol | 2-chloroacetic acid |
| 34 | 4-(3,5-dibromopyridyl-2-oxy) phenol | 2-bromopropanoic acid |
| 35 | 4-(3,5-dichloropyridyl-2-oxy) phenol | methyl 2-chloroacetate |
| 36 | 4-(5-chloropyridyl-2-oxy) phenol | methyl 2-bromopropanoate |
| 37 | 4-(3,5-diiodopyridyl-2-oxy) phenol | ethyl 2-bromopropanoate |

TABLE 1

| Example | Product Phenoxycarboxylic acid derivative | Physical property | Yield (%) |
|---|---|---|---|
| 3 | ethyl 4-[4-(4-trifluoromethylphenoxy) phenoxy]-2-pentenoate | $n_D^{20}$ 1.5195 | 96.0 |
| 4 | 4-[4-(4-trifluoromethylphenoxy) phenoxy]-2-pentenoic acid | $n_D^{20}$ 1.5119 | 91.2 |
| 5 | 2-[4-(4-trifluoromethylphenoxy) phenoxy]propanoic acid | m.p. 136–138° C. | 90.5 |
| 6 | ethyl 4-[4-(4-trifluoromethylphenoxy) phenoxy]pentanoate | $n_D^{20}$ 1.5080 | 94.5 |
| 7 | ethyl 4-[4-(4-trifluoromethylphenoxy) phenoxy]pentanoate | $n_D^{20}$ 1.5103 | 95.0 |
| 8 | octyl 4-[4-(4-trifluoromethylphenoxy) phenoxy]-2-pentenoate | $n_D^{20}$ 1.5045 | 96.5 |
| 9 | ethyl 4-[4-(3-trifluoromethylphenoxy) phenoxy]-2-pentenoate | $n_D^{20}$ 1.5155 | 96.0 |
| 10 | 4-[4-(2-chloro-4-trifluoromethylphenoxy) phenoxy]-2-pentenoic acid | m.p. 88–89° C. | 87.3 |
| 11 | ethyl 4-[4-(2-nitro-4-trifluoromethylphenoxy) phenoxy]-2-pentenoate | $n_D^{20}$ 1.5343 | 95.6 |
| 12 | ethyl 4-[4-(2-bromo-4-trifluoromethylphenoxy) phenoxy]-2-pentenoate | $n_D^{20}$ 1.5341 | 96.0 |
| 13 | 4-(4-phenoxyphenoxy)-2-pentenoate | m.p. 113–114° C. | 94.7 |
| 14 | butyl 4-[4-(2-chlorophenoxy) phenoxy]-2-pentenoate | $n_D^{20}$ 1.5547 | 95.1 |
| 15 | ethyl 4-[4-(4-cyanophenoxy) phenoxy]-2-pentenoate | $n_D^{20}$ 1.5625 | 93.7 |
| 16 | ethyl 2-[4-(2,4-dichlorophenoxy) phenoxy]propanoate | $n_D^{20}$ 1.5601 | 90.0 |
| 17 | isopropyl 2-[4-(2-nitro-4-chlorophenoxy) phenoxy]propanoate | $n_D^{20}$ 1.5605 | 97.1 |
| 18 | ethyl 2-[4-(2-chloro-4-nitrophenoxy) phenoxy]acetate | m.p. 92–95° C. | 97.0 |
| 19 | ethyl 4-[4-(2-nitro-4-chlorophenoxy) phenoxy]-2-butenoate | $n_D^{20}$ 1.5790 | 97.5 |
| 20 | ethyl 2-[2-(4-nitrophenoxy) phenoxy]butanoate | $n_D^{20}$ 1.5701 | 94.3 |
| 21 | isopropyl 4-[4-(4-bromophenoxy) phenoxy]-2-pentenoate | $n_D^{20}$ 1.5724 | 95.0 |
| 22 | ethyl 2-[4-(3,5-dichloropyridyl-2-oxy) phenoxy]propanoate | $n_D^{20}$ 1.5603 | 90.2 |
| 23 | butyl 4-[4-(3,5-dichloropyridyl-2-oxy) phenoxy]-2-pentenoate | $n_D^{20}$ 1.5565 | 92.7 |
| 24 | ethyl 2-[4-(5-nitropyridyl-2-oxy) phenoxy]propanoate | $n_D^{20}$ 1.5557 | 91.3 |
| 25 | ethyl 4-[4-(5-nitropyridyl-2-oxy) phenoxy]-2-pentenoate | $n_D^{20}$ 1.5684 | 89.2 |
| 26 | methyl 4-(4-phenoxyphenoxy)-3-methy-2-butenoate | m.p. 55–56° C. | 91.0 |
| 27 | isopropyl 4-[4-(4-chlorophenoxy) phenoxy]-3-methyl-2-butenoate | m.p. 49–50° C. | 98.0 |
| 28 | 2-[4-(5-methyl-2-isopropylphenoxy) phenoxy]propanoic acid | m.p. 91–92° C. | 91.1 |
| 29 | 2-[4-(3-methylphenoxy) phenoxy] propanoic acid | m.p. 78–79° C. | 92.5 |
| 30 | 2-[4-(4-chloro-3-methylphenoxy) phenoxy]propanoic acid | m.p. 128–129° C. | 90.5 |
| 31 | isobutyl 2-[4-(4-trifluoromethylphenoxy) phenoxy]propanoate | m.p. 55–57° C. | 90.8 |
| 32 | ethyl 2-[4-(2-bromo-4-trifluoromethylphenoxy) phenoxy]propanoate | $n_D^{20}$ 1.5541 | 91.1 |
| 33 | 2-[4-(5-bromopyridyl-2-oxy) phenoxy]acetic acid | m.p. 130–132° C. | 93.1 |
| 34 | 2-[4-(3,5-dibromopyridyl-2-oxy) phenoxy]propanoic acid | m.p. 68–70° C. | 90.3 |
| 35 | methyl 2-[4-(3,5-dichloropyridyl-2-oxy) phenoxy]acetate | m.p. 52–54° C. | 93.7 |
| 36 | methyl 2-[4-(5-chloropyridyl-2-oxy) phenoxy]propanoate | m.p. 88–90° C. | 92.0 |
| 37 | ethyl 2-[4-(3,5-diiodopyridyl-2-oxy) phenoxy]propanoate | m.p. 85–87° C. | 90.0 |

EXAMPLES 38 TO 48

In accordance with the process of Example 1 except replacing tributylethylammonium bromide by the other quaternary ammonium salt or phosphonium salt shown in Table 2, ethyl 4-[4-(4-trifluoromethylphenoxy)-phenoxy]-2-pentenoate was produced. The results are shown in Table 2.

TABLE 2

| Example | Quaternary salt | Yield (%) |
|---|---|---|
| 38 | benzyltrimethylammonium chloride | 93.5 |
| 39 | benzyltriethylammonium bromide | 95.2 |
| 40 | benzyltrioctylammonium chloride | 94.1 |
| 41 | benzyltriphenylphosphonium chloride | 94.7 |
| 42 | tetraethylammonium bromide | 94.5 |
| 43 | tetrabutylammonium bromide | 94.5 |
| 44 | tetrahexylammonium bromide | 93.2 |
| 45 | trioctylmethylammonium chloride | 94.1 |
| 46 | tetrabutylphosphonium bromide | 95.0 |
| 47 | methyltriphenylphosphonium bromide | 94.7 |
| 48 | butyltriphenylphosphonium bromide | 94.3 |

EXAMPLES 49 TO 56

In accordance with the process of Example 1 except replacing chlorobenzene by the other nonpolar solvent shown in Table 3, ethyl 4-[4-(4-trifluoromethylphenoxy)phenoxy]-2-pentenoate was produced. The results are shown in Table 3.

TABLE 3

| Example | Solvent | Yield (%) |
|---|---|---|
| 49 | benzene | 95.0 |
| 50 | toluene | 95.1 |
| 51 | xylene | 94.7 |
| 52 | dichlorobenzene | 94.5 |
| 53 | chloroform | 94.0 |
| 54 | carbon tetrachloride | 94.1 |
| 55 | n-hexane | 94.0 |
| 56 | cyclohexane | 93.7 |

EXAMPLE 57

In accordance with the process of Example 1 except using 67.0 g (0.412 mole) ethyl 4-chloro-2-pentenoate instead of 85.4 g (0.412 mole) of ethyl 4-bromo-2-pentenoate, ethyl 4-[4-(4-trifluoromethylphenoxy)phenoxy]-2-pentenoate was obtained. The yield was 83.4%.

We claim:

1. In a process for producing a phenoxycarboxylic acid derivative having the formula

wherein R represents

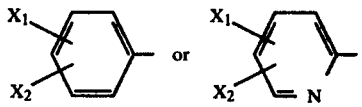

and $X_1$ represents a hydrogen atom, a halogen atom, a lower alkyl group, trifluoromethyl group, nitro group or cyano group and $X_2$ represents a hydrogen atom, a halogen atom, a lower alkyl group, nitro group or cyano group, R' represents

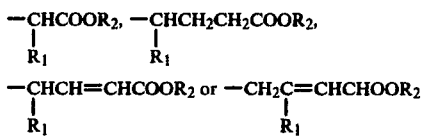

And $R_1$ and $R_2$ are the same and different and respectively represent hydrogen atom or a lower alkyl group, by reacting a phenol compound having the formula $$RO-\text{\textlangle}\text{\textrangle}-OH \quad (I)$$

with a halogen compound having $$X-R' \quad (II)$$

wherein X represents a halogen atom, in the presence of a base the improvement comprising carrying out the reaction in the presence of a quaternary phosphonium salt selected from the group consisting of benzyltrialkylammonium salts, benzyltrialylphosphonium salts, tetraalkylammonium salts, tetraalkylphosphonium salts, triphenylalkylphosphonium salts and triphenylbenzylphosphonium salts in a nonpolar solvent at 50° to 90° C., the molar ratio of the quaternary ammonium salt or quaternary phosphonium salt to the phenol compound is from 0.005 to 0.05 and the molar ratio of the base to the phenol compound is from 0.05 to 1.5.

2. A process according to claim 1 wherein said base is an alkali metal compound or an alkaline earth metal compound.

* * * * *

UNITED STATES PATENT AND TRADEMARK OFFICE
CERTIFICATE OF CORRECTION

PATENT NO. : 4,254,262
DATED : March 3, 1981
INVENTOR(S) : Koike et al

It is certified that error appears in the above-identified patent and that said Letters Patent are hereby corrected as shown below:

Column 10, line 25, after "of" insert

--a quaternary ammonium salt or --.

Column 10, line 27, delete "benzyltrialylphosphonium" and insert --benzyltrialkylphosphonium--.

Signed and Sealed this

Eighteenth Day of August 1981

[SEAL]

Attest:

GERALD J. MOSSINGHOFF

Attesting Officer    Commissioner of Patents and Trademarks